United States Patent [19]

Sewell

[11] Patent Number: 5,217,687
[45] Date of Patent: Jun. 8, 1993

[54] STERILIZING APPARATUS AND METHOD FOR STERILIZING INFECTIOUS WASTE MATERIALS

[75] Inventor: Kenneth R. Sewell, Columbus, Ohio

[73] Assignee: Iso-Spectrum, Inc., Columbus, Ohio

[21] Appl. No.: 709,309

[22] Filed: Jun. 3, 1991

[51] Int. Cl.$^5$ .............................................. A61L 2/12
[52] U.S. Cl. ...................................... 422/21; 422/22; 423/DIG. 18
[58] Field of Search ............. 422/22, 21; 423/DIG. 8, 423/DIG. 20

[56] References Cited

U.S. PATENT DOCUMENTS

| | | | |
|---|---|---|---|
| 3,366,564 | 1/1968 | Allen | 422/22 |
| 3,522,167 | 7/1970 | Allen | 422/22 |
| 3,594,115 | 9/1963 | Wesley et al. | 422/22 |
| 3,617,178 | 11/1971 | Clouston | 422/22 |
| 4,458,153 | 7/1984 | Wesley | 422/22 |

*Primary Examiner*—Robert J. Warden
*Assistant Examiner*—Laura E. Collins
*Attorney, Agent, or Firm*—Levy, Zito & Grandinetti

[57] ABSTRACT

The invention includes a pressure vessel and a method of pressurizing, via a fluid medium, waste matter at an ultra high pressure. The invention includes an ultra high pressure vessel. The pressure vessel has quick opening closures at each end. A fluid medium is available for supply to pressure vessel cavity within the pressure vessel. A means for supplying the fluid medium under ultra high pressures into the fluid vessel cavity is also provided. The invention further includes a ram means or a means for loading and compacting the waste matter. The method includes pressurizing the matter at a sufficient pressure and holding the pressure for a sufficient time to sterilize the matter.

1 Claim, 3 Drawing Sheets

STERILIZING APPARATUS AND METHOD FOR STERILIZING INFECTIOUS WASTE MATERIALS

BACKGROUND

1. Field of the Invention

The invention relates to an apparatus and a method for sterilizing components, matter and infectious waste materials using an ultra high pressure vessel and a fluid medium to apply isostatic pressure to the matter or waste material. Specifically, the invention relates to an apparatus and a method for sterilizing matter and especially, organic matter such as infectious waste materials using ultra high isostatic pressure.

2. Description of the Background Art

Growing concern for the environment is having a major impact on the cost of sterilizing medical or infectious waste materials. Increases in health care and medical technology, combined with an increasing life span for the average person, have resulted in large increases in the number of hospital patents and production of infectious waste materials. Currently, the average hospital patient generate between 2.8 and 3 pounds of medical waste per day. Up to about 15 percent of this matter is defined as "infectious". Recent occurrences of infectious waste materials washing up on U.S. beaches and the growing fear of AIDS are increasing the public's concern over sterilization and disposal of medical waste materials.

Federal and State regulations require the sterilization of all infectious waste materials prior to disposal. Current methods of sterilization include incineration, mechanical and chemical treatment, steam/compaction, and microwave shredding. Incineration is a widely accepted method of disposal of infectious waste materials. Advantages of this method include the acceptability of the procedure by regulatory agencies, high volume reduction (about 90 percent of the material is destroyed), and the conversion of the waste into an unrecognizable state. However, incineration poses a series of problems. Incinerators have maintenance and operational difficulties, temperature variability, licensing and permit requirements, air emissions problems, and ash disposal problems. Operational costs, such as labor, maintenance, and fuel expenses, combine to make incineration one of the most costly methods of sterilization with processing costs averaging 8 to 9 cents per pound and 2 cents per pound for disposal. Many states now require emission scrubbers to improve air emissions. However, scrubbers also require a source of water, which presents an additional problem in states suffering from water shortages. The requirement of new pollution monitoring equipment and concern over the pollutants produced from burning plastic infectious waste disposal bags further add to incineration disadvantages.

Another accepted method of infectious waste disposal is the mechanical and chemical treatment of infectious waste materials. Advantages of this method of treatment include the acceptability of such processed materials by land fills, unrecognizable materials, high dilution and volume ratios, process on demand cycles, no order, and no air emissions. Disadvantages of this method of treatment include specialized personnel training, consumable parts, suspended solids, storage and handling of chlorine, some regulatory problems, and a frequent requirement for sewer permits. Materials are processed at a rate of 5 cents per pound and 1 cent per pound for disposal.

Steam/Compaction treatment of matter is a generally accepted procedure for general matter and infectious waste materials. Advantages of this method include a 5:1 volume reduction, easy operation, no double handling of materials, no air emissions, no licensing or permits. Disadvantages of this method of treatment include the land fill acceptability, long cycle time, requirement for validation and monitoring equipment, and odor. The cost for processing matter by this method averages 4 cents per pound and 2 cents per pound for disposal. This method has difficulty effectively sterilizing the entire spectrum of microbes.

One of the newest methods of sterilization is microwave shredding of waste matter. Advantages of this method of treatment include rendering the waste unrecognizable, an 8:1 volume reduction, no liquid effluent, no air emissions, and easy operation. Disadvantages of this method of treatment include long delivery dates for new equipment, replacement of consumable parts, restrictions on waste content, such as metals and moisture, long hold times, odor, and low destruction quality. Processing costs average 7 cents to 10 cents per pound and disposal costs are not determined at this time.

The sterilization of infectious waste materials encounters a number of additional problems than those problems identified above. Most of the above listed technologies cannot be scaled down to a size and cost of acquisition and operation that fits the low volume producers of infectious waste materials such private hospitals. Strict procedures and regulations governing the transportation of hazardous waste materials from a producer to a central disposal site significantly adds to the cost of the disposal. This cost averages about 6 cents per pound.

Currently, the industry is lacking an apparatus and a method for sterilizing matter, including infectious waste materials, that is environmentally acceptable, cost effective, and can be scaled to meet the needs of either larger or small waste producers.

SUMMARY OF THE INVENTION

The invention includes an ultra high pressure vessel. The pressure vessel has quick opening closures at each end. A fluid medium is available for supply to a pressure vessel cavity within the pressure vessel. A means for supplying the fluid medium under ultra high pressures into the fluid vessel cavity is also provided. The invention further includes a ram means or means for loading and compacting the waste matter, that is being processed in the pressure vessel cavity. The apparatus, desirably, includes means for controlling the pressurization and hold time required to sterilize a material. The invention is a portable unit for mobile use at different sites for producers of infectious waste materials. The invention includes at least one ram to remove the matter from the pressure vessel.

The method of this invention includes pressurizing matter and holding the matter under sufficient pressure for sufficient time to sterilize the matter. The term sterilization for purposes of this invention is a condition of the pressurized matter wherein substantially all cellular, microbial and viral life in the matter is destroyed.

DETAILED DESCRIPTION OF THE INVENTION

The invention is an apparatus and a method for sterilizing components, matter, and organic matter such as infectious waste materials. The apparatus includes an ultra high pressure vessel. The pressure vessel has quick opening closures at each end. A fluid medium is available for supply to a pressure vessel cavity within the pressure vessel. A means for supplying the fluid medium under ultra high pressures into the fluid vessel cavity is also provided. The invention can further include a means for loading and compacting the waste matter, that is being processed into the pressure vessel cavity. The apparatus includes means for controlling the pressurization to sterilize a material. The invention is a portable unit for mobile use at different sites for producers of infectious waste materials. The method of this invention includes pressurizing matter and holding the matte under sufficient pressure for sufficient time to sterilize the matter. The term sterilization for purposes of this invention is a condition of the pressurized matter wherein substantially all cellular, microbial and viral life in the matter is destroyed.

Figure 1:
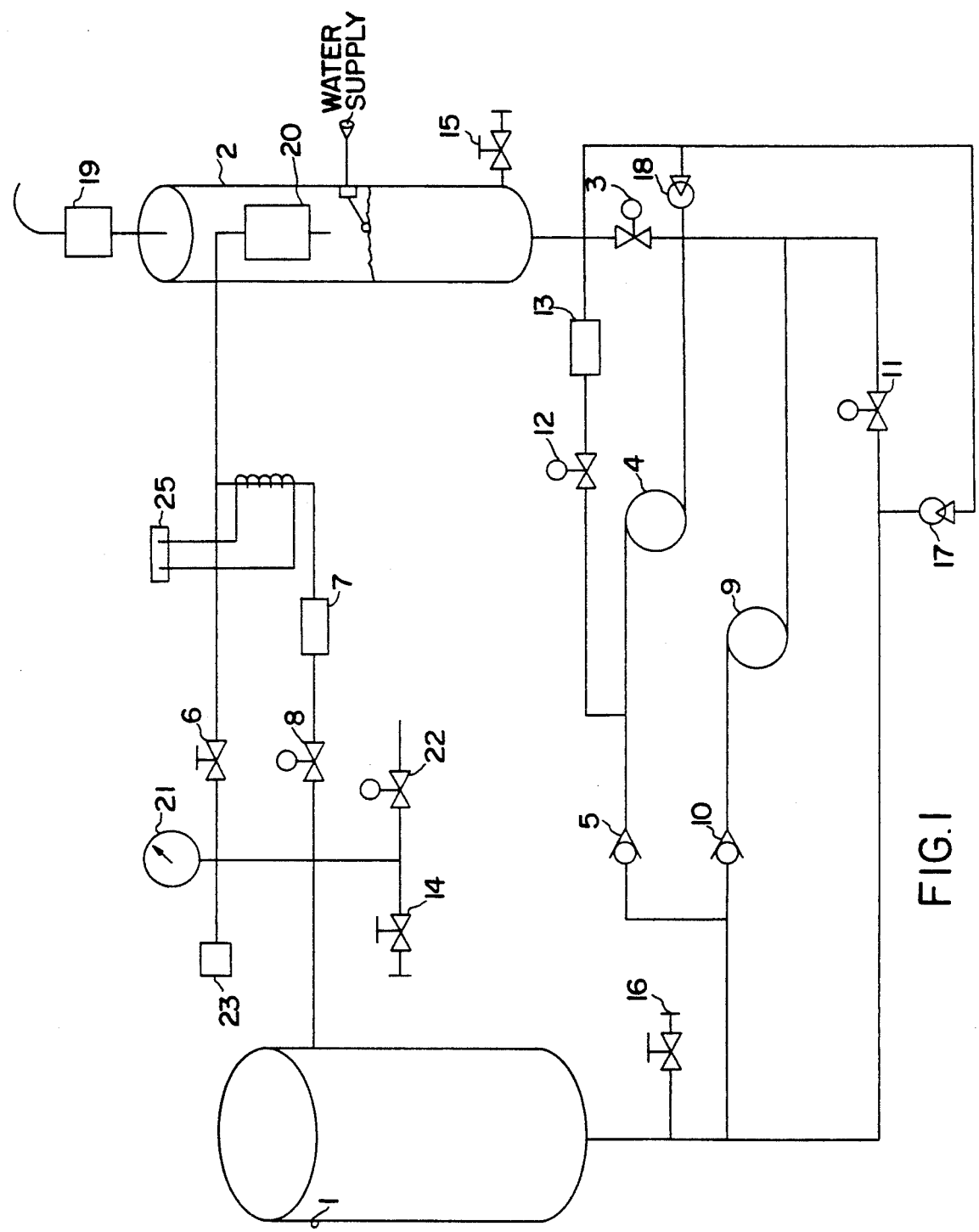
FIG. 1 illustrates a block diagram of the preferred embodiment of the pressure vessel and major components of this invention utilizing a liquid fluid medium.

FIG. 1 illustrates a pressure vessel 1 and the other major components of the invention. A fluid medium storage reservoir 2 contains a fluid medium. Desirable fluid mediums are common tap water or tap water with elevated amount of chlorine. The fluid medium is transported through a low pressure valve 3 to a high volume/low pressure pump 4. The pressure of the fluid medium is slightly increased and directed though a check valve 5 into the pressure vessel 1. Displaced air is directed out the top vent line and though a high pressure vent valve 6 and a flow switch 7 into the reservoir 2. In the unlikely event of airborne microbes, a biological filter located on the reservoir filters 20 for displaced air. Once the flow switch senses fluid flow, high pressure valve 8 closes, the high volume/low pressure 4 stops pumping, and high pressure pump 9 beings pumping the medium through check valve 10 into the pressure vessel 1. Pressure inside the pressure 1 is increased by the pumping action of the high pressure pump 9. Once the desired pressure is sensed by the mechanical gauge and/or pressure transducer, the high pressure pump 9 is stopped. The pressure vessel 1 then holds the pressure for a pre-specified dwell time which is a time sufficient to substantially sterilize the matter. When the hold time expires, pressure is lowered by venting fluid through 8 and flow switch 7 into the storage reservoir 2. The fluid used to transmit the pressure to the matter is also sterilized in the process. Fluid is removed from the pressure vessel 1 by opening high pressure valve 11 and low pressure valve 12 and closing low pressure valve 3. This action directs fluid medium from the pressure vessel 1 to the suction of the high volume/low pressure pump 4, and the pump discharges to the reservoir.

The apparatus of FIG. 1 desirably includes a variety of valves, switches, and gauges. The apparatus includes flow switch 13, chemical injection valves 14, 15, and 16, relief valves 17 and 18, and biological air filters 19 and 20. Also, gauge 21, air vent 22, and transducer 23. Cold isostatic presses can be operated by hand. Desirably, cold isostatic presses have a means for controlling 25 that can be programmed to sterilize a variety infectious waster materials at different pressures and hold times.

Figure 2:
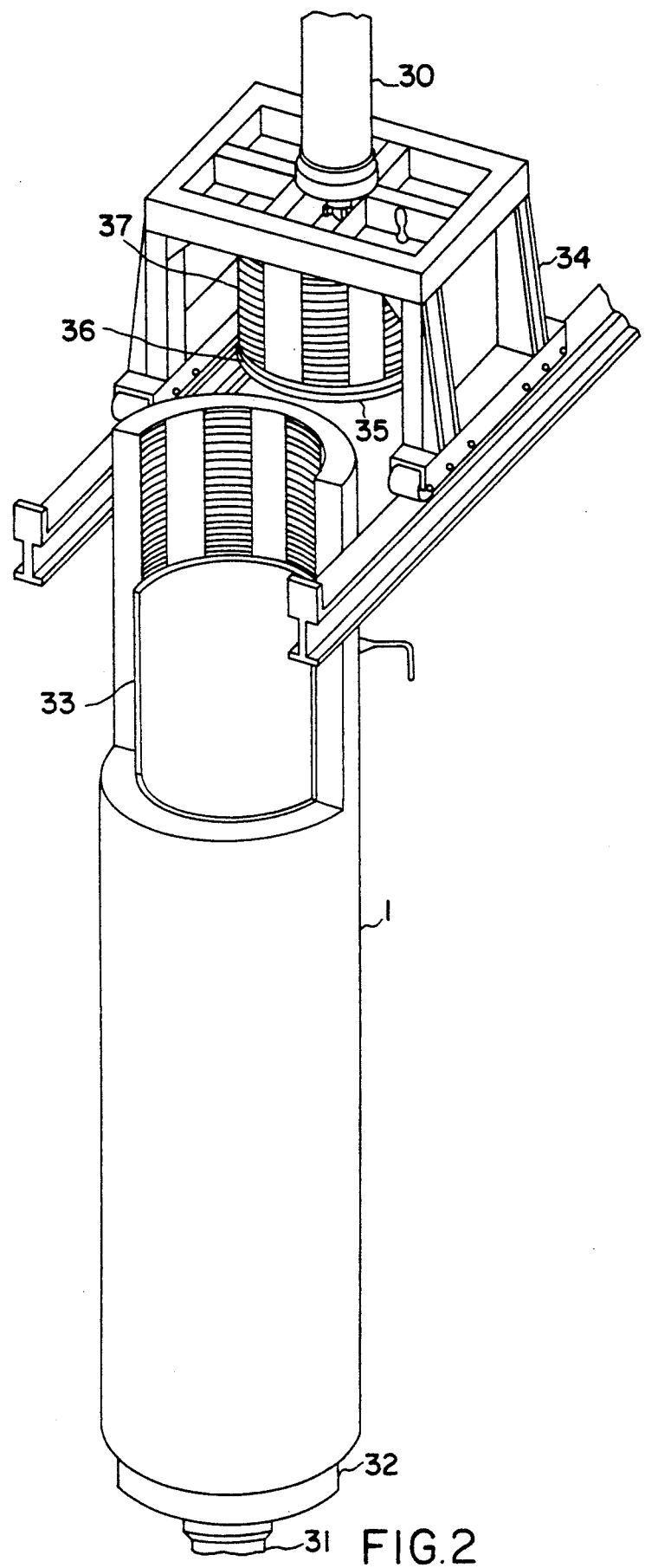
FIG. 2 illustrates a cross sectional view of a pressure vessel according to this invention.

FIG. 2 illustrates the pressure vessel with its novel ram shaft assembly 30 and lower closure ram shaft 31. The apparatus has a lower closure assembly 32 and a metal processing "can" or container 33. The novel upper closure assembly 34 has an upper ram plate 35, seal 36, and upper closure nut 37.

FIG. 2 further illustrates the insertion of a metal processing can 33 located inside of the pressure vessel 1. Sealed polymer bags (not shown) containing infectious waste materials are loaded into the metal processing can 33 and then inserted into the pressure vessel 1. The upper closure assembly 34 is then inserted into the pressure vessel shell and locked shut with an ⅛ turn.

Figure 3:
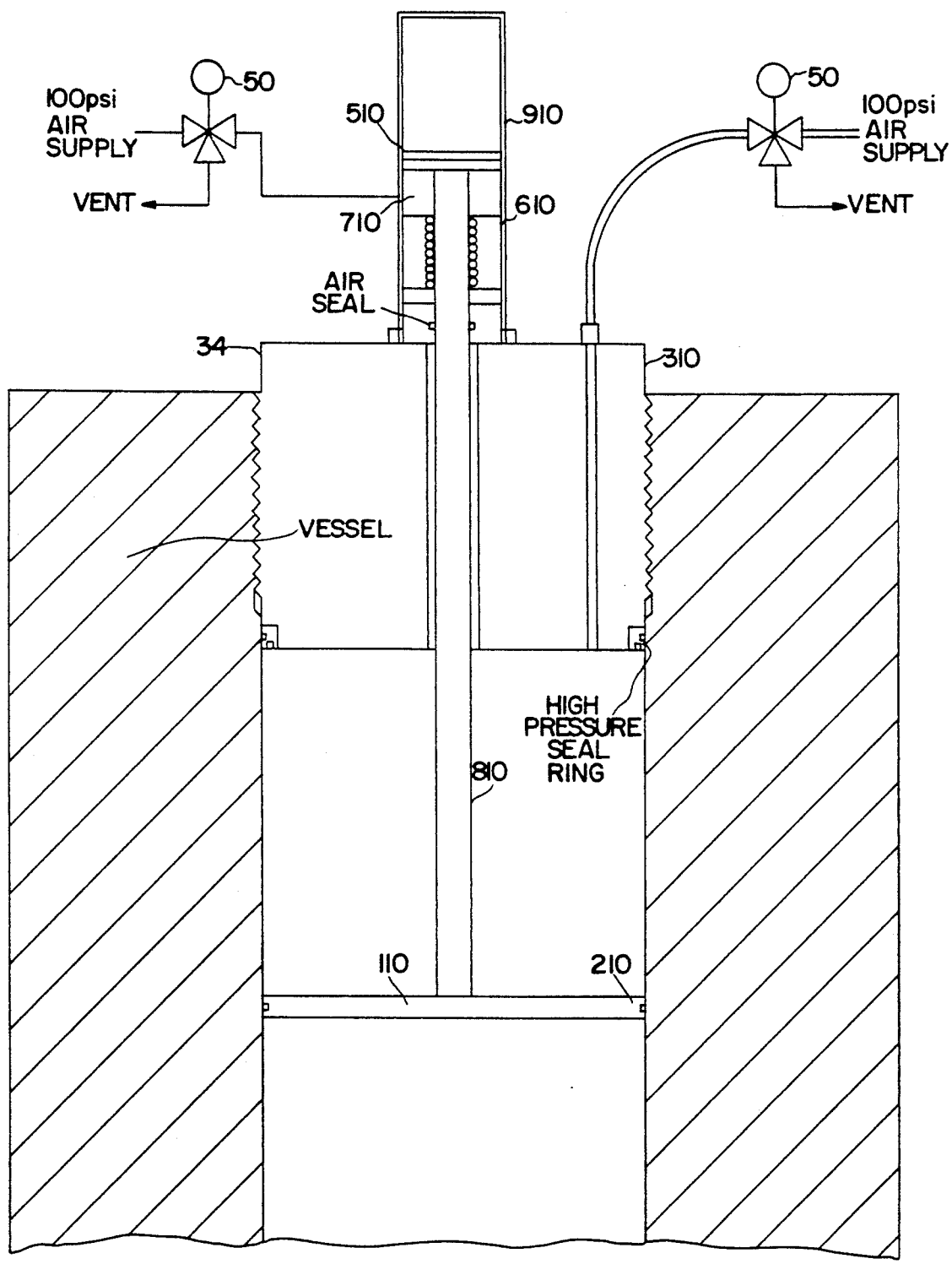
FIG. 3 illustrates a cross sectional view of the upper closure showing a compaction ram.

FIG. 3 illustrates a cut away section of the upper closure assembly 34 of the pressure vessel 1. The bottom of the upper closure assembly 34 includes a flat plate 110 with pressure seals 210 attached to the side to the plate 110. The center of the plate 110 is attached to a shaft 810 that passes through the center of the upper closure nut 310. The shaft 810 then protrudes into a sealed shaft housing 910. On top of the shaft 810 is a smaller flat sealed plate 510. The shafts alignment is guided by journal bearings 610 located in the top and bottom of the shaft housing 910. Air is introduced between the lower steel plate 110 and closure 310 by opening at least one three way low pressure valve 50 pressurizing the area between the plate 110 and closure nut 310. The force of the air drives the plate 110 downward compacting the materials loaded into the pressure vessel 1. Air displaced by the movement of the ram passes through high pressure valve 11 and low pressure valve 3 to the reservoir 2. As pressure builds up in the reservoir 2 the air passes through the biological filter 20 to the atmosphere. The three way low pressure valve 50 then shifts the pressurizing of the upper section of the cylinder. Air located in the section between the lower plate 110 and the closure nut 310 is then vented through the reservoir biological filter 20. The ram means provided by the upper closure assembly 34 is retracted by pressurizing the section 710 below the top seal plate 510. The ram means is designed to maintain a positive air pressure to prevent leakage of air contaminated with infectious waste materials. The total density of the matter placed in the pressure vessel can be determined by the travel of the ram or ram means. The operator has the option of opening the upper closure assembly 34 and loading additional matter. Once a full load is achieved the pressure vessel 1 is ready for pressurization.

Once the excess fluid has been removed from the pressure vessel a ram similar to the one on the upper closure assembly 34 lifts the can 33 clear of the pressure vessel shell (not shown) where it is lifted clear of the pressure vessel 1 allowing the insertion of another processing can. The processed matter is removed from the pressure vessel 1 and the further processed by shredding, compaction and/or disposed of in a land fill.

The apparatus desirably includes a means for controlling the pressurization and hold time required to sterilize an infectious waste material. Such a means for controlling is desirably. A microprocessor and Programmable Logic Controller (PLC). The microprocessor can be programmed with a series of segments. Each segment performs a specific task.

Segment 1 activates a contact referred to as "event number one." This signal is then transferred to the PLC which activates a solenoid that activates the hydraulic piston that lowers the upper closure assembly 34 into place. Once the closure nut 310 is in place, a first proximity sensors in the upper closure assembly 34 can send a signal to the PLC triggering another second signal that activates the solenoid for a hydraulic cylinder that turns the closure nut 310 and locks it into place. a second proximity sensor can send a verification signal to the PLC which advances the microprocessor to the next segment 2.

Segments 2 is event two which closes a microprocessor contact that sends a signal to the PLC activating the solenoid that positions the three way air valve or the compaction ram in the down position compacting the matter in the pressure vessel 1. Proximity sensors located in the shaft shell can monitor the position of the shaft. After a brief period of non-movement, the combination of signals from the proximity sensors sent to the PLC determine if the ram was retracted and the upper closure nut 310 removed for the addition of matter of if continuation of the sterilization process occurred.

Segment 3 occurs in the microprocessor when the position of the ram indicates a full vessel. This event sends a signal to the PLC that retracts the ram. A signal from the proximity sensor then signals the PLC which sends an open signal to high pressure valve 6 and low pressure valve 3 and the high volume/low pressure pump 4. A signal from the flow switch 7 shuts high pressure valve 8, stops the high volume/low pressure pump 4 and starts the high pressure pump 9. Pressure is monitored by a mechanical gauge 21 with electrical contact switches and a pressure transducer 23 which sends a signal to a digital panel meter (not shown) with set point alarms. When a signal is received from each pressure monitor a signal is sent to the PLC stopping the high pressure pump 9, shutting the low pressure valve 3, and advancing the microprocessor to segment 4.

Segment 4 occurs in the microprocessor when the unit remains pressurized for a short period of time. During this time, pressure is monitored by the pressure instruments. If pressure drops below 5 percent of programmed level, the high pressure pump 9 is activated to restore pressure to the programmed pressure.

If the cycle includes the use of a heated fluid medium, thermocouples located inside the pressure vessel 1 are used to monitor the temperature of the fluid medium during the hold segment. Program variables that include longer dwell times and/or higher programs can be activated if the unit fails to maintain a temperature that guarantees sterilization.

Segment 5 activates event 4 which closes a contact and sends a signal to the PLC activating high pressure valve 8. This action vents the pressure vessel 1 to atmospheric level. A signal is sent from the digital panel meter (low pressure) set point alarm. The PLC advances the program to segment 6.

Segment 6 occurs when the microprocessor activates event 5 which sends a signal to the PLC (1) opening high pressure, valves and low pressure valve 12, (2) closing low pressure valve 3 and starting the high volume/low pressure pump 4, and (3) removing the fluid medium from the pressure vessel 1. Flow switch 13 is used to verify completion of the fluid transfer and signal the PLC to shift to segment 7.

Segment 7 occurs when the microprocessor activates event 6 which reverses signals and the PLC unlocks, opens, and retracts the upper closure assembly 34. Once verification of closure retraction is made, the PLC advances the program to segment 8.

Segment 8 occurs when the microprocessor extends and lifts the metal processing can so it can be removed from the pressure vessel 1.

If a component failure prevents the completion of a sterilization cycle, access ports in the piping system and pressure vessel 1 can allow the addition of chemical sterilization agents. These agents can be circulated using the high volume/low pressure pump 4 to ensure sterilization. Upon completion of the chemical sterilization process the matter can be removed and repairs to the apparatus can be performed.

The system can also utilize a heated fluid medium to enhance the effects of the high pressure. Shorter hold time and/or lower pressures can be used when the processing fluid is heated. Heating of the fluid can occur in the reservoir. The heat source, desirably, consists of electric heating elements attached to the reservoir body. A temperature control relay can receive input from sealed thermocouples located in wells throughout the reservoir.

Pressure vessel is equipped with means for controlling or various sensors for monitoring the pressure and pressure holding time of the fluid medium and/or material within the pressure vessel. The material being processed is placed inside of the pressure vessel and initially packed by a loading mechanism. Pressure vessel is sealed and a fluid medium is pumped into the pressure vessel and displaces any remaining air. The pressure of the fluid medium is to a sufficient pressure to substantially sterilize the matter. Desirably, the pressure is increased to a level between 45,000 psi and 80,000 psi, which effectively kills 99.99% of all microbes or other living matter contained within the pressure vessel. The fluid medium is then pumped out of the pressure vessel and the matter is removed for mechanical compaction, shredding, or disposal in a land fill. Sufficient hold times can be instantaneous to 1 or more hours depending upon the pressure used or amount of heat applied, if any.

The method of this invention includes pressurizing matter and holding the matter under sufficient pressure for sufficient time to sterilize the matter. The term sterilization for purposes of this invention is a condition of the pressurized matter wherein substantially all cellular, microbial and viral life in the matter is destroyed. Process pressures will range between 40,000 psi and 80,000 psi depending on hold times and the matter being processed. Higher pressures require less hold time to sterilize matter, but can require a more expensive pressure vessel. The use of a heated fluid medium decreases the amount of pressure and/or hold time required to substantially sterilize an infectious waste matter.

All air discharges, that occur during the process, are desirably, vented through the reservoir biological filter and vent 19. All fluids located inside the pressure boundary are sterilized by the high pressure. The reservoir sized to expand a majority of the fluid medium into the pressure vessel during the pressurization cycle. This procedure prevents any accumulation of microbes in the reservoir tank. Residual fluid removed with processed infectious waste materials is replaced by tap water or chlorinated water in the reservoir 2.

The preferred embodiment of the invention is performed to sterilize medical waste materials.

To conserve storage space, compaction of medical waste is required. Compaction is achieved by removing the air from the plastic bags containing medical waste products. This procedure is also required to achieve minimum sterilization process times. Since air will compress at a higher rate than liquid, pumping times are extended when large concentrations of air are left in the plastic bags.

Experiments conducted with this invention used plastic bags containing simulated medical waste products. The bags were evacuated and simultaneously sealed using a modified food packaging machine. Volume reductions up to 70 percent were achieved on samples containing low density materials such as gauze, cloth, and bandages. Objects made of glass and metal can be sterilized by processing the items in special containers. Metal containers, glass and sharp items can also be simultaneously compacted and sterilized by inserting a metal foil liner inside the plastic container.

Liquid wastes are processed in the same manner as solid wastes. Liquid wastes can be placed in a plastic soda container with a flexible diaphragm sealed across the opening to prevent leakage. Upon removal from the sterilizer, hard plastic lids can be attached to the openings without breaking the diaphragm, thereby securing the containers for transportation. After processing, packages are removed from the pressure vessel and placed in appropriate shipping containers for dry, non-refrigerated storage.

A desirable feature of this invention is its ability to be designed in a size or scale of equipment to best suite the user. The basic design is capable of being increased to a size suitable for processing several thousand pounds per hour. Of waste or reduced in size for a small dental or medical office. The apparatus of this invention can be designed to apply uniaxial pressure. Such designs are similar to "hot presses". The apparatus of this invention can be made portable by being placed on a small truck. Other embodiments of the invention use microwaves to heat and/or destroy organic matter.

I claim:

1. A method for sterilizing matter comprising:

pressurizing matter at a pressure between about 45,000 and about 80,000 pounds per square inch in a pressure vessel, said pressure being applied isostatically through a fluid medium;

applying microwave energy within said pressure vessel to said pressurizing matter;

mainintaining isostatic pressure and the application of microwave energy for a sufficient time to sterilize said pressurizing matter;

terminating said application of microwave energy; and releasing said isostatic pressure.

* * * * *